United States Patent
Schwind et al.

(10) Patent No.: US 7,794,654 B2
(45) Date of Patent: Sep. 14, 2010

(54) METHOD FOR THE SELECTIVE STERILIZATION OF DIAGNOSTIC TEST ELEMENTS

(75) Inventors: Karin Schwind, Schifferstadt (DE);
Wolfgang Fiedler, Laudenbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/620,931

(22) Filed: Jan. 8, 2007

(65) Prior Publication Data

US 2007/0176120 A1 Aug. 2, 2007

Related U.S. Application Data

(63) Continuation of application No. PCT/EP2005/007335, filed on Jul. 7, 2005.

(30) Foreign Application Priority Data

Jul. 9, 2004 (DE) .......................... 10 2004 033219

(51) Int. Cl.
*C12Q 1/68* (2006.01)
(52) U.S. Cl. .................. 422/50; 600/583; 250/492.1
(58) Field of Classification Search .................. 600/583; 250/492.1, 492.3; 206/305; 422/22, 1
See application file for complete search history.

(56) References Cited

U.S. PATENT DOCUMENTS

| 4,442,836 | A | | 4/1984 | Meinecke et al. |
| 4,981,649 | A | * | 1/1991 | Shibauchi et al. ............. 422/24 |
| 5,009,654 | A | | 4/1991 | Minshall et al. |
| 5,318,584 | A | | 6/1994 | Lange et al. |
| 5,496,302 | A | | 3/1996 | Minshall et al. |
| 5,554,166 | A | | 9/1996 | Lange et al. |
| 6,143,164 | A | | 11/2000 | Heller et al. |
| 6,191,424 | B1 | | 2/2001 | Stirling et al. |

(Continued)

FOREIGN PATENT DOCUMENTS

DE 10134650 7/2001

(Continued)

OTHER PUBLICATIONS

International Patent Application PCT/EP2005/007335 Search Report and Written Opinion Report mailed Oct. 12, 2005.

*Primary Examiner*—Max Hindenburg
*Assistant Examiner*—Renee Danega
(74) *Attorney, Agent, or Firm*—Woodard, Emhardt, Moriarty, McNett & Henry LLP (57) ABSTRACT

The invention concerns a method for producing integrated, diagnostic test elements (1) which have a lancing area (2) and a detection area (3). The lancing area is used to generate an opening in the skin and the detection area is used to detect an analyte in a body fluid. The selective sterilization sterilizes the lancing area but not the detection area by electron radiation. The method according to the invention comprises the steps of screening the detection area on the test element against electron radiation and subsequently irradiating the test element with electron radiation. The invention additionally concerns a method according to the invention in which the test elements and lancing areas are in a connected arrangement and are brought into the radiation area by moving the entire arrangement. Finally the invention concerns a diagnostic test element which has been produced according to the inventive method.

14 Claims, 7 Drawing Sheets

U.S. PATENT DOCUMENTS

| | | |
|---|---|---|
| 6,315,738 B1 | 11/2001 | Nishikawa et al. |
| 6,520,326 B2 | 2/2003 | McIvor et al. |
| 6,572,566 B2 | 6/2003 | Effenhauser |
| 6,594,156 B1 * | 7/2003 | Van Antwerp et al. ...... 361/816 |
| 6,653,096 B1 * | 11/2003 | Christensen et al. .......... 435/31 |
| 6,880,242 B2 * | 4/2005 | Van Antwerp et al. ........ 29/832 |
| 7,192,405 B2 * | 3/2007 | DeNuzzio et al. ........... 600/583 |
| 2002/0155267 A1 * | 10/2002 | Bader ......................... 428/216 |
| 2003/0050573 A1 * | 3/2003 | Kuhr et al. .................. 600/567 |
| 2003/0153939 A1 | 8/2003 | Fritz et al. |
| 2003/0211619 A1 * | 11/2003 | Olson et al. .................. 436/44 |
| 2004/0106941 A1 | 6/2004 | Roe et al. |
| 2007/0191736 A1 * | 8/2007 | Alden ......................... 600/583 |

FOREIGN PATENT DOCUMENTS

| | | |
|---|---|---|
| DE | 10142232 | 3/2003 |
| EP | 0199484 | 10/1986 |
| EP | 0425602 B1 | 5/1991 |
| EP | 0565970 B1 | 6/1994 |
| EP | 1285629 A1 | 2/2003 |
| EP | 1360931 A1 | 11/2003 |
| EP | 1402812 A1 | 3/2004 |
| JP | 09-311205 * | 10/1997 |
| WO | WO90/11095 A2 | 10/1990 |
| WO | WO98/48695 A1 | 11/1998 |
| WO | WO01/66010 A1 | 9/2001 |
| WO | WO02/056751 A2 | 7/2002 |
| WO | WO03/089028 * | 4/2003 |

* cited by examiner

METHOD FOR THE SELECTIVE STERILIZATION OF DIAGNOSTIC TEST ELEMENTS

CROSS-REFERENCE TO RELATED APPLICATIONS

This application is a continuation of International Application No. PCT/EP2005/007335 filed Jul. 7, 2005, published on Jan. 19, 2006 as WO 2006/005503 A1, which claims priority to German Application DE 10 2004 033 219.3 filed Jul. 9, 2004, which are hereby incorporated by reference in their entirety.

BACKGROUND

1. Technical Field

The present invention concerns a method for producing diagnostic test elements for the detection of analytes in body fluids. The invention additionally concerns diagnostic test elements which have been produced by such a method.

2. General Introduction

The examination of body fluids enables an early and reliable detection of pathological states in clinical diagnostics as well as the selective and well-founded control of physical conditions. Nowadays a few microliters down to less than 1 microliter blood are often all that is required for individual analyses that are specifically directed towards one parameter. In order to collect blood a sterile, sharp lancet is pierced through the skin for example into the finger pad or the earlobe of the person to be examined. This method is especially suitable when the blood sample can be analysed immediately after blood collection.

Carrier-bound rapid tests have become established for the chemical and biochemical analysis of body fluids in laboratories specialized for this purpose and in particular also for use outside permanent laboratories. Based on a specially developed dry chemistry such carrier-bound rapid tests can be carried out simply and in an uncomplicated manner even by laymen despite the often complex reactions involving sensitive reagents. The most prominent example of carrier-bound rapid tests are test strips for determining the blood glucose content in diabetics.

In the diagnostic tests that are used nowadays for the detection of an analyte (e.g. blood glucose) in a body fluid (e.g. blood) the function of lancing to generate a skin opening and the detection function are usually divided among several components e.g. a lancing aid for lancing and generating a drop of blood and an analytical device e.g. a test strip for taking up the drop of blood, passing the blood from the uptake site to the detection area and the detection of an analyte e.g. blood glucose.

Lancets and suitable devices for them which enable blood to be collected in as painless and reliable a manner as possible are offered especially in the field of so-called home-monitoring i.e. in a field where medical laymen themselves carry out simple analyses of the blood and in this case in particular for the regular blood collection by diabetics that has to be carried out several times daily to control the blood glucose concentration. Examples of lancets and lancing aids are the commercially available devices (lancing aids) and lancets Glucolet® from Bayer AG and Softclix® from Roche Diagnostics GmbH. Such lancets and devices are for example the subject matter of WO 98/48695, EP 0,565,970, U.S. Pat. Nos. 4,442,836 or 5,554,166.

The self-determination of blood sugar is nowadays a method that is used world-wide in diabetes monitoring. Blood sugar devices in the prior art such as e.g. Accu-Check Sensor® (from Roche Diagnostics) consist of a measuring device into which a test element (test strip) is inserted. The test strip is contacted with a drop of blood which has previously been collected from a finger pad by means of a lancing aid. The numerous system components (lancet, lancing aid, test strip and measuring device) require a lot of space and give rise to a relatively complex handling. There are now also systems with a higher degree of integration and thus a simpler handling. These for example include Accu Check Compact® (from Roche Diagnostics), the Glucometer Dex (from Bayer Diagnostics) and the Soft-Sense (from Medisense). In the two former systems the test strips are stored in the measuring device and thus provided for measurement.

A next step in miniaturization can for example be achieved by integrating several functions or functional elements in a single diagnostic test element. For example the operating sequence can be considerably simplified by suitably combining the lancing process and sensory analyte concentration detection in one assembly. Such lancing—measuring disposables which are also referred to in the following as integrated test elements are not yet available on the market but are described for example in DE 101 34 650, U.S. Pat. No. 6,572,566, EP 0,199,484 and U.S. Pat No. 6,143,164.

3. State of the Art

The basic problem with the manufacture of the above-mentioned integrated test elements in which the lancing area and detection area are combined in one assembly is that, on the one hand, the lancing area must be sterile since it comes into contact with the skin or penetrates into the body and, on the other hand, the sensitive detection chemistry in the detection area must not be damaged by the manufacturing process.

U.S. Pat. No. 6,520,326 describes for example the sterilization of an integrated test element in which the entire sensor is sterilized and in particular the lancing and also the detection area. It attempts to reduce damage to the detection chemistry in the detection area by a special selection of the detection chemistry.

In DE 101 42 232 several connected lancets in the form of a tape are manufactured and a second tape on which the detection areas are located is produced in parallel. The lancet tape is sterilized, then combined with the second tape and finally the test elements are separated.

The method described in the state of the art U.S. Pat. No. 6,520,326 has the disadvantage that when selecting the detection chemistry it must be ensured that it is insensitive to sterilization. It appears questionable whether such a method can be realized at all and to what extent an adequate performance in particular with regard to sensitivity and reproducibility can be achieved under these circumstances.

In the case of the manufacturing process described in DE 101 42 232 an additional effort is required to produce two parallel tapes and to accurately fit together the lancing area and detection area.

Object

The object of the present invention is to overcome the disadvantages of the prior art as well as the problems mentioned above. In particular it is the object of the present invention to provide a compact integrated diagnostic test element that can be manufactured in high numbers in which the lancing area is sterile and the detection chemistry in the detection area is functional.

SUMMARY

The present invention concerns a method for sterilizing integrated test elements consisting of at least one detection area which is sterilized and at least one lancing area that is protected from the sterilization, as well as test elements which are produced by such a method.

The integrated test elements for the detection of an analyte in a body fluid consist of two areas with different requirements: the lancing area to generate a skin opening and the detection area. The lancing area must be sterile to ensure that during lancing the test element does not carry germs into the body of the user whereas the detection area must not be exposed to the sterilization since the sterilization damages the detection chemistry that is located in the detection area.

Integrated test elements promise to be a major advance in the further development of test systems towards more operating convenience, lower requirement for body fluid for the detection and a more rapid detection. This results in a great increase in the ease of use and a simplified handling since the user only has to place the test elements on a body site and lance himself. The analyte is subsequently transported into the detection area and measured there.

Since sterile and unsterile areas are integrated on a disposable in the case of integrated test elements, it was found that it is particularly advantageous to manufacture the test elements as completely as possible and then to screen the unsterile areas during the sterilization. This simplifies the manufacturing process especially for the lancing—measuring disposables described above.

There are basically several known methods for sterilizing lancing areas and in particular for sterilizing lancets made of metal or plastic. One method is irradiation with gamma radiation. Another method is steam sterilization for example with ethylene oxide (ETO). It was found that both gamma radiation and ETO sterilization have the disadvantage that very complicated measures are required in this case to protect the detection area from sterilization and thus from an inactivation. Thick lead plates have to be used in order to adequately shield gamma radiation but even then one has the problem of diffraction of the radiation which leads to the additional irradiation of components that are located behind a shield. Hence selective sterilization is very complicated especially when the area to be irradiated is very close to the area which is not to be irradiated such as is the case especially for integrated test elements. For an ETO sterilization the detection area must, on the one hand, be packaged in a gas-tight manner and additionally the sterilization space has to be sealed gas-tight against the environment which can only be achieved in a very complicated manner especially in the case of assembly-line production. Moreover, the two methods are very difficult to integrate into an assembly-line production as is commonly used for components that are produced in high numbers.

It was found that electron radiation is particularly suitable for the selective sterilization according to the invention since it is, on the one hand, suitable for sterilizing metal objects such as lancets and, on the other hand, it can be screened relatively simply for example in order to protect the detection area. Thus a suitable dose of sterilizing electron radiation can for example be screened almost completely and preferably by a factor of 1000 by a 2 to 5 mm thick metal plate for example made of steel, copper, aluminium or lead whereas almost 100% of the sterilizing radiation penetrates plastic layers having a thickness of several millimeters. Moreover, electron radiation sterilization has the advantage that it can be carried out in a dry manner, rapidly and at low temperature and can be readily integrated into an assembly-line production. Thus test elements according to the invention can be economically manufactured in large numbers.

Hence, in principle, all previously known variants of detection areas and lancing areas can be used for the selective sterilization of diagnostic test elements. Since the detection area is protected from irradiation during the sterilization, no additional stabilizers have to be added to the detection chemistry. In most cases these additives reduce the performance of the detection chemistry.

Furthermore, the lancing area can be provided with a protection made of plastic especially already before the sterilization since the electron radiation adequately penetrates the plastic and sterilizes the lancet underneath and the plastic protects the lancing area from re-contamination. An advantage of the method according to the invention is that the manufacture does not have to take place in a clean room which considerably reduces the production outlay and costs.

In this manner it is possible to sterilize the lancing area and at the same time to protect the detection chemistry in the detection area from the sterilizing radiation even in the case of integrated test elements in which the lancing area and detection area are combined in one assembly or on one component. Hence, test elements produced by the method according to the invention can be miniaturized in a simpler manner and are therefore particularly well-suited for use in compact diagnostic test systems.

Selective sterilization within the scope of the present invention describes methods in which certain areas of a product and in particular the lancing area are selectively sterilized while other defined areas of the product and in particular the detection area are not sterilized.

Hence selective sterilization means a spatial selection in the sense of a selection between irradiated and non-irradiated areas and in particular does not mean that areas irradiated with electron radiation are only sterilized selectively in the sense of partially i.e. that only certain germs are killed.

A diagnostic test element is understood as any form of carrier-bound rapid test for diagnostics and especially rapid tests in a strip form, so-called test strips, and in this case especially for determining the blood glucose content in diabetics.

The term lancing area circumscribes the area of the test element that is used to make an opening in the skin through which the body fluid e.g. blood or interstitial fluid escapes. One possible design of a lancing area is the front part of a lancet. The lancing area is in contact with or in the direct vicinity of the opening that is to be made in the skin and must be sterile in order to prevent germs from the lancing area entering the body. The discharge of body fluid can if necessary be accelerated by supporting measures for example by generating a vacuum.

The test zone describes the area in which the detection chemistry is located that is used to detect an analyte. The detection area is located within this test zone. The detection area denotes the area in which the analyte is also actually measured to determine the concentration. Since the detection chemistry is usually damaged by electron radiation, it must be ensured that the detection area is not exposed to electron radiation during the selective sterilization. Thus for example the screening can be selected such that although parts of the test zone are irradiated for example to ensure that the lancing area and possibly also the transport element are completely sterilized, the detection area is, however, considerably less irradiated. The sterilizing radiation could preferably be screened almost completely and preferably by a factor of 1000.

Analyte means a component of the body fluid that reacts in the detection area with the detection chemistry such that—above a certain amount of the analyte—the reaction can be measured in a measuring arrangement. A preferred embodiment comprises using blood as the sample liquid and detecting blood glucose as the analyte in the detection area and thus determining the concentration of blood glucose.

In addition to blood interstitial fluid and other endogenous fluids are also possible as body fluids. It is also possible to detect not only one analyte e.g. blood glucose but also several analytes e.g. HBA1C and to carry out this detection in one body fluid e.g. blood as well as in a mixture of several body fluids e.g. blood plus interstitial fluid.

With regard to wavelength, energy content and radiation dose, the electron radiation used should be selected such that a sterilization of the lancing area of the test elements is guaranteed.

A preferred embodiment of the method according to the invention for the selective sterilization of test elements comprises screening the detection area from electron radiation while the test element is irradiated with electron radiation resulting in the sterilization of the lancing area.

The entire test element including the screen can be irradiated with electron radiation during the sterilization. In each case it must be ensured that the lancing area is irradiated to such an extent that it is sterile after the process step.

Screening the detection area is to be understood as any means which ensures that the detection area on the test element is screened from the electron radiation used to such an extent that the detection chemistry located in the detection area is functional after the sterilization step. Screening plates or diaphragms preferably made of metal are a preferred embodiment of screening. In particular lead, iron, copper and aluminium as well as alloys thereof are very suitable screening materials. The screen can for example be located between the source of electron radiation and test element right next to the transport tape on which the test elements are guided along in a directed manner. The screen can, however, also be arranged near to the source of electron radiation and in particular the diaphragm of the source of electron radiation can be used to direct the radiation emerging from the radiation source only onto the area to be sterilized and in particular onto the lancing area while the area to be protected and in particular the detection area is screened from the radiation.

In another embodiment the screen is located directly at or on the test element where it screens the detection area. This screen preferably also prevents germs from escaping from the unsterile detection area. This embodiment has the additional advantage that after sterilization the lancing area does not have to be sealed by a protection against contamination from the detection area e.g. via the air. In the case of sterilization by electron radiation, this screen of the detection area can be a metal foil or metal-plastic foil which for example is applied in an air-tight manner by welding the plastic foil with the plastic of the test element. Subsequently the entire test element is for example exposed to the sterilizing radiation in the process of which it is of course nevertheless selectively sterilized due to the local screening of the detection area.

Another embodiment comprises providing the detection area with a protection against the escape of germs e.g. a plastic foil which prevents germs from unsterile areas and in particular from the detection area from reaching the lancing area via the air route although the said foil does not screen off the sterilizing radiation or at least not to an adequate extent. If necessary this protection is sterilized at least on the outside preferably with plasma treatment; afterwards the detection area and protection are screened against electron radiation with a screen e.g. a metal plate, and the lancing area is sterilized with electron radiation. This embodiment has the additional advantage that it may be possible to dispense with an additional protection of the lancing area. For example the detection area on the test elements is sealed with a plastic foil and the test elements are sealed individually in a package e.g. a container without an additional protection of the lancing area.

The electron rays can act on the test element from one or from several sides; accordingly the screen may if necessary be composed of one or more parts in order to screen the radiation from all necessary sides. If an irradiation from several sides is necessary, either several radiation sources can act on the test element simultaneously or successively from various sides, or one radiation source acts on several sides of the test element, or the test element is moved e.g. turned in the path of the rays or is guided through the path of the rays several times in different orientations such that the lancing area is completely sterilized.

The irradiation with electron radiation can take place such that each test element is individually screened and sterilized or such that an arrangement of several test elements is screened and subsequently the entire arrangement is irradiated. Another method of screening is that the test elements are arranged in a package and the package is designed such that the detection area of the test elements is screened from electron radiation and the entire package is screened. A preferred embodiment of the package is a container for storing the test elements e.g. a drum in which several test elements are arranged individually in chambers in an axially symmetrical manner, or a box in which the test elements are stacked or arranged in a matrix-like manner. A screen such as a metal plate is integrated into the package in the region of the detection area. For example the lower area of a plastic drum is coated with metal. In another embodiment the container itself has no screen, but stands in a holder which serves as the screen and has been placed in corresponding wells such as a metal plate with round holes into which the drum is inserted exactly so far that the detection area of the test elements in the drum is screened by the holder while the lancing area can be irradiated.

If the test elements are in a closed package during sterilization, the package is preferably designed such that the packaging material, preferably plastic and cardboard, is permeable to the electron radiation and at the same time resistant to the irradiation to such an extent that also after the sterilization it fulfils the requirements for the packaging especially with regard to stability and shelf-life of the imprint.

The packaging used for the selective sterilization can either already be the final packaging or a primary and transport packaging which serves to transport the test elements from one process step to the next during production.

Another embodiment of the invention is that the test elements are moved into the irradiation area of a radiation source by a feeding device. The feeding device preferably comprises a transport tape or a belt on which the test elements are arranged preferably in a directed orientation. The feeding device transports the test elements into the area of the sterilization e.g. an electron radiation chamber or an irradiation tunnel and subsequently to the next production step.

Another variant of the method is that the test elements or their packages are connected and that the test elements are brought into the radiation area by moving the connected arrangement. For example the diagnostic test element can be made of a tape material as described in DE 101 42 232. In this case lancing areas e.g. the lancets that are combined to form a tape or belt, and detection areas e.g. test strips that are combined to form a tape or belt are provided. The two tapes are combined and the lancing area tape is glued to the detection area tape. After the lancing areas have been sterilized while screening the detection areas, the connected tapes are separated into individual test elements for example by cutting off the terminal test elements.

In a further embodiment the detection areas are applied directly to the lancing area tape e.g. by printing. Subsequently the detection areas are screened and the test element tape is selectively sterilized and separated.

Another object of the invention is a test element according to the invention in which at least the area of the lancing area which penetrates the skin is sealed with a protection which prevents penetration of germs. Protection in this connection means any suitable means which, on the one hand, ensures that the lancing area can be sterilized with an electron beam and remains sterile after the sterilization and, on the other hand, prevents accidental lancing of the user when the test element is handled. A preferred embodiment of a lancing area protection is protection by a cap known in the prior art such as that which is present on Softclix lancets. The cap completely encloses the lancing area and thus prevents penetration of germs. The cap is preferably already applied to the lancing area before sterilization e.g. moulded on or attached. In order to ensure that germs that may be present in the lancing area or on the inside of the cap are rendered harmless in the subsequent sterilization, it is essential in this procedure that the protective material is sufficiently permeable to the sterilizing electron radiation.

Another preferred feature of the invention is that the lancing area protection is made of a pierceable material or is removed from the lancing area before use. Elastic material can be used in particular as a pierceable material.

Figure 7:
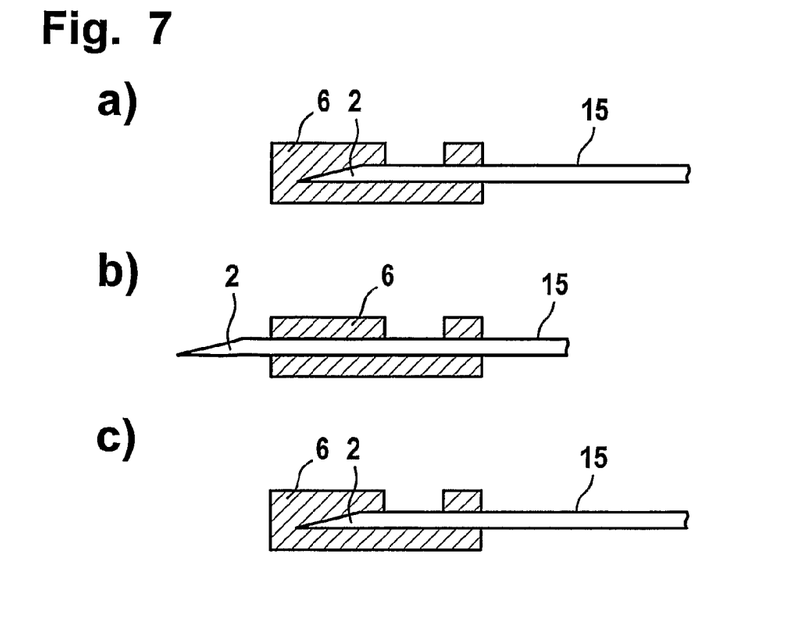
FIG. 7 Lancing area protection made of pierceable material.

WO 01/66010, which is hereby incorporated by reference, for example describes a lancet (15) whose lancing area (2) which in this case is referred to as the lancet tip, is completely surrounded by a lancing area protection (6), a so-called lancet body, which is manufactured from an elastic material (see FIG. 7*a*). During the lancing the lancet tip (2) pierces the lancing area protection (6, FIG. 7*b*). After the lancing the lancet tip (2) retracts and is again enclosed by the lancing area protection (6) (FIG. 7*c*). Such an embodiment of the sealing of the lancing area can be used advantageously for the integrated test elements according to the invention.

The protection of the lancing area is preferably designed such that the lancing area is again completely surrounded by the protection after use. In this way accidental injury to the user or other persons can be avoided.

A preferred embodiment describes a lancing area e.g. a lancet tip which pierces the protection e.g. a thermoplastic elastomer during lancing and retracts again into the protection after the lancing. In an alternative embodiment the protection e.g. a plastic cap is manually removed or removed by the test device before lancing. After use the protection is again placed on the lancing area and the test element is disposed off without a lancing area protection.

An optional feature of the invention concerns a transport element which is arranged between the lancing area and detection area and is used to transport the analyte from the lancing area to the detection area. After an opening in the skin has been made by the lancing area of the test element, a sample of the body fluid e.g. blood is collected and the analyte e.g. blood glucose is transported to the detection area in order to be analysed there. Thus, the function of the transport element is to transport the analyte or several analytes, if several analytes are to be detected, from the lancing area to the detection area. Capillary force is usually used as the driving force for transport. Various embodiments are conceivable for the structure of the transport element. For example the transport element can have a capillary. The transport element preferably comprises a capillary channel or a capillary gap, but it is also possible to use a type of wick. The transport element may be a separate component e.g. an additional capillary or it can be integrated into the component of the lancing area or detection area for example in the form of a groove in the lancet or as a capillary channel on a test strip. Furthermore, the transport element can of course also be integrated into another component of the test element and in particular also into the protection of the lancing area.

The amount of body fluid required to detect an analyte can be considerably reduced in a test element according to the invention because the transport path from the lancing area to the detection area is considerably shortened by integrating lancing and detection on one component. Since the majority of the body fluid is required to wet the transport path and only a small proportion is necessary for the actual detection of an analyte, the shortening of the transport path reduces the required amount of body fluid. Another advantage of shortening the transport path is that the body fluid to be examined is transported more rapidly into the detection area at the same flow rate, e.g. due to capillary forces, which accelerates the entire process for detecting an analyte.

The present invention encompasses a method for producing a diagnostic test element according to the above-mentioned features by means of selective sterilization as well as a diagnostic test element that is directly manufactured according to the method of the invention and in particular according to the above-mentioned preferred embodiments.

BRIEF DESCRIPTION OF THE DRAWINGS

The invention is further elucidated by the following figures.

numerals in the figures denote:
1 diagnostic test element
2 lancing area
3 detection area
4 sterilizing electron radiation
5 screening of the detection area
6 protection of the lancing area
7 test zone
8 germ protection
9 primary packaging for test elements
10 holder for primary packaging 11 part to be protected
12 part to be irradiated
13 outer packaging
14 transport tape
15 lancet
16 pooling area
17 capillary channel or gap
18 subchannels
19 collecting foil
20 skin
21 skin opening
22 test element base plate

DESCRIPTION OF SELECTED EMBODIMENTS

Figure 1:
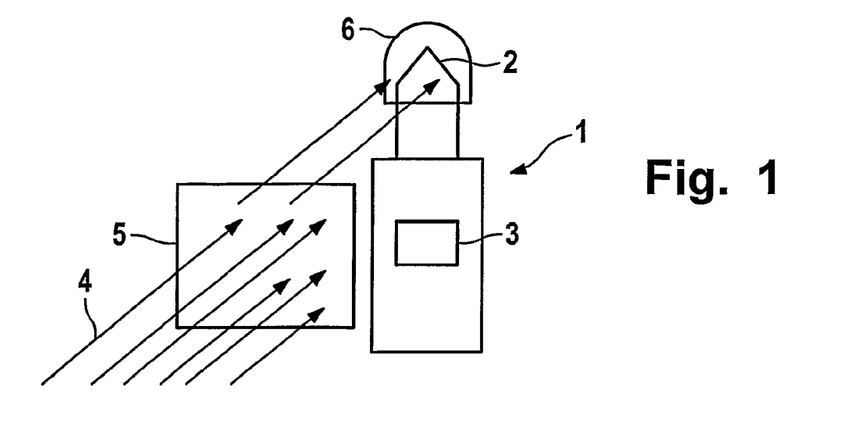
FIG. 1 Selective sterilization of a diagnostic test element with a lancing area protection.

FIG. 1 shows schematically an embodiment of the method for selective sterilization. The figure shows a diagnostic test element (1) with a lancing area (2) and a detection area (3) where the test element (1) is sterilized by electron radiation (4). In this case the screen (5) screens the detection area (3) in such a manner that the detection area (3) is not sterilized in order to prevent the sterilization from damaging the detection chemistry and in particular the enzymes present in the detection area (3). The lancing area (2) is sealed with a protection (6) which prevents entry of germs. The protection (6) is permeable to the sterilizing electron radiation (4) and thus allows a sterilization of the lancing area (2) even when the protection (6) is in place and at the same time ensures that the lancing area (2) remains sterile after the sterilization until its intended use.

Figure 2:
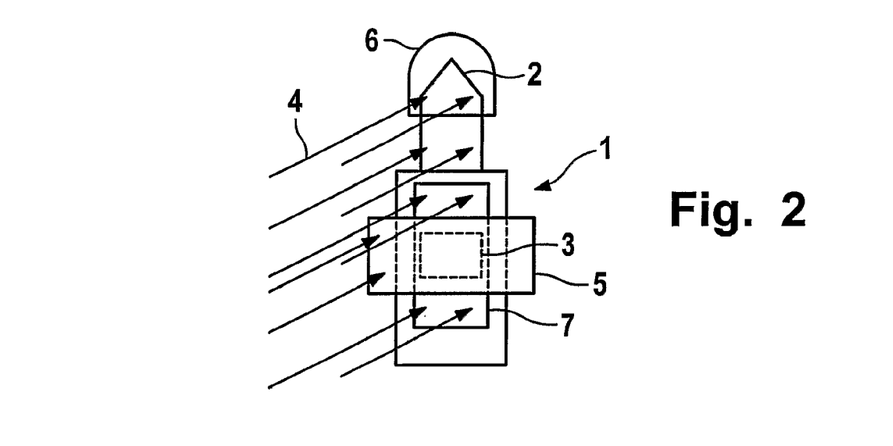
FIG. 2 Selective sterilization of a diagnostic test element with a partially irradiated test FIG. 3 Diagnostic test element with germ protection.

FIG. 2 shows another embodiment of the method according to the invention. In this case the test zone (7) on which the detection chemistry is located is considerably larger than the detection area (3) which delineates the area in which the analyte is actually detected. The screen (5) completely covers the detection area (3), but the test zone (7) is only partially screened. The lancing area (2) is completely sealed by a protection (6) which prevents entry of germs. Accordingly during the subsequent sterilization with electron radiation (4) the detection chemistry which is located in the unprotected area of the test zone is also irradiated in addition to the lancing area (2). However, the resulting damage to the detection chemistry in this area is irrelevant to the detection of the analyte since only the reaction of the analyte with the detection chemistry in the detection area (3) is taken into account for the measurement.

Figure 3:
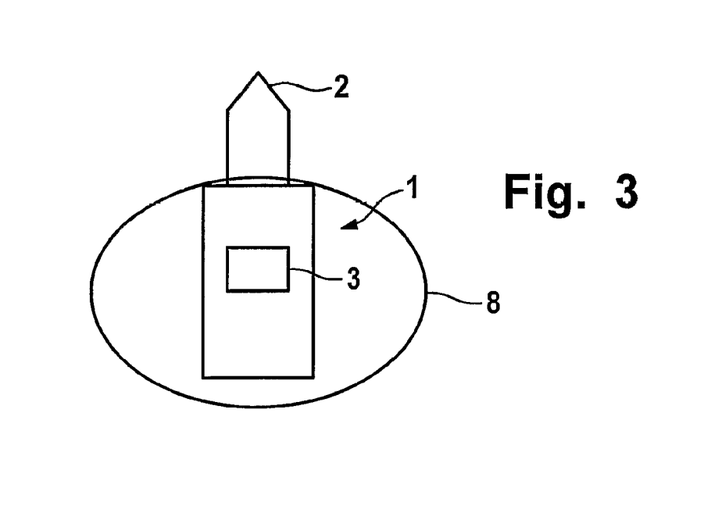

FIG. 3 shows another embodiment of the method according to the invention. In this case the detection area (3) is provided with a protection against the escape of germs (8) and for this reason the lancing area (2) is not protected. Subsequently the test element (1) is placed in a primary packaging (9) for example similarly to FIGS. 5b-d, the detection areas are screened and the lancing areas are irradiated. In a preferred manner the test elements are individually packaged within the primary packaging e.g. they are placed or individually sealed in individual chambers within the packaging such that when a test element is removed the sterility of the other test elements is ensured.

Figure 4:
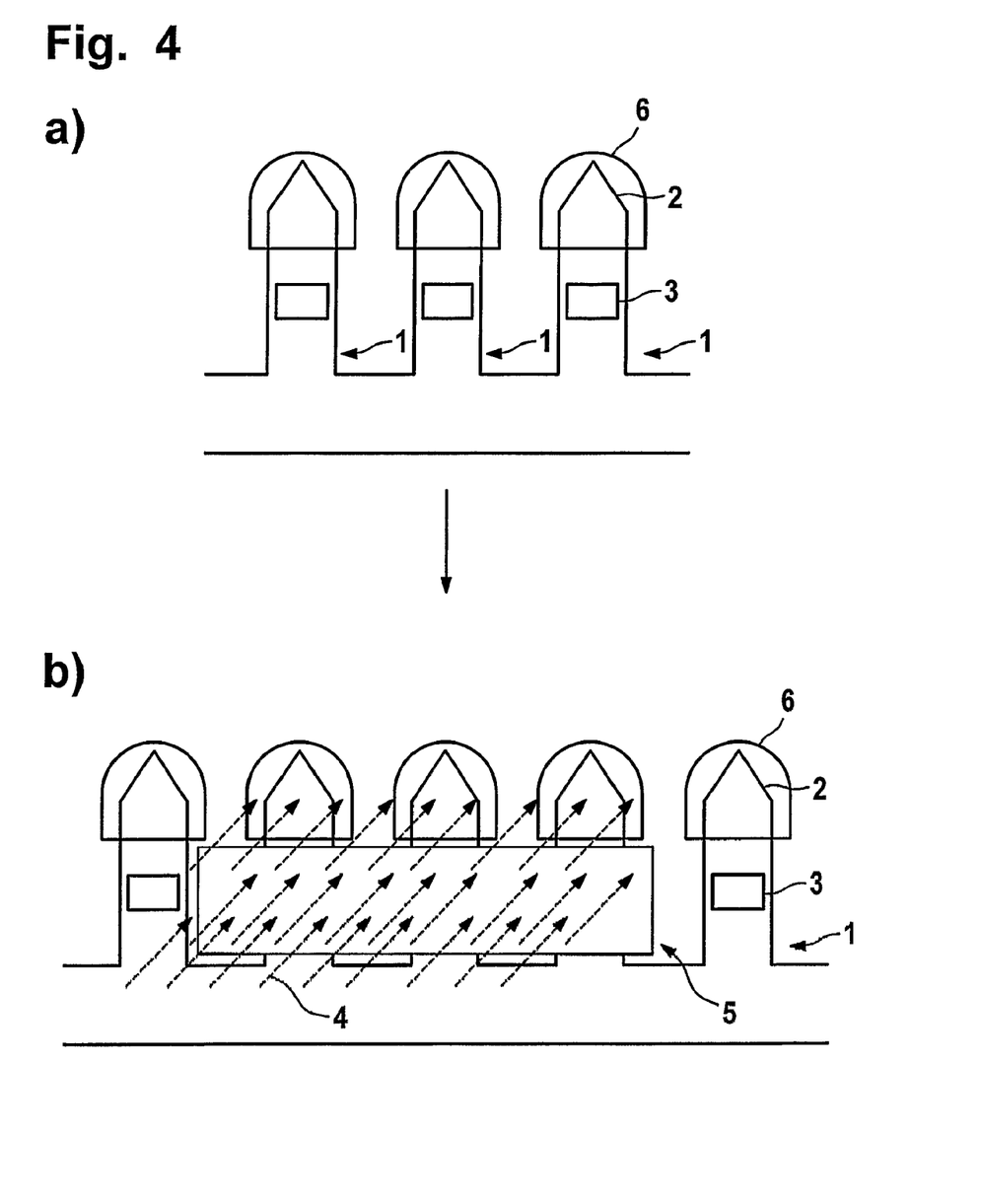
FIG. 4 Selective sterilization of connected diagnostic test elements.

FIG. 4 shows another embodiment of the method according to the invention. In FIG. 4a connected test elements (1) with a lancing area (2) and detection area (3) are shown where the lancing area (2) is provided with a protection (6). FIG. 4b shows the arrangement illustrated in FIG. 4a during selective sterilization. The electron radiation (4) irradiates the connected test elements (1) while the respective detection area (3) is protected from the irradiation (4) by a screen (5).

Figure 5:
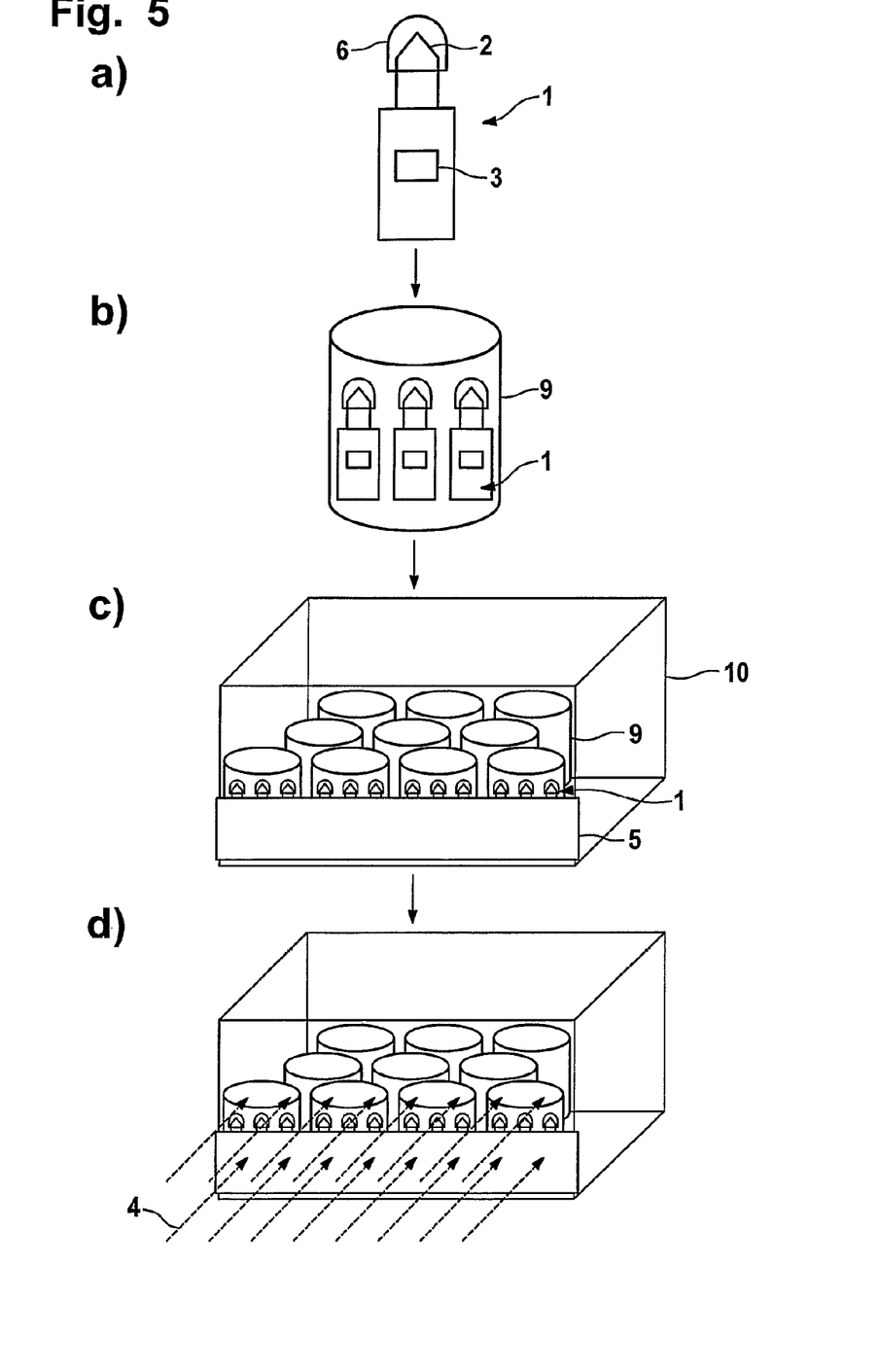
FIG. 5 Selective sterilization of diagnostic test elements in a package.

FIG. 5 shows another embodiment of the method according to the invention. FIG. 5a shows a test element (1) with a lancing area (2), detection area (3) and protection of the lancing area (6) which is packaged in an oriented manner together with several test elements in a primary package (9) e.g. a container or a drum. Subsequently several primary packages (9) are placed in FIG. 5c in a holder (10) which has a screen (5) that is designed such that in the subsequent irradiation with electron radiation (4) according to FIG. 5d all detection areas (3) are protected from the radiation (4) and at the same time all lancing areas (2) are sterilized by the electron radiation (4).

Figure 6:
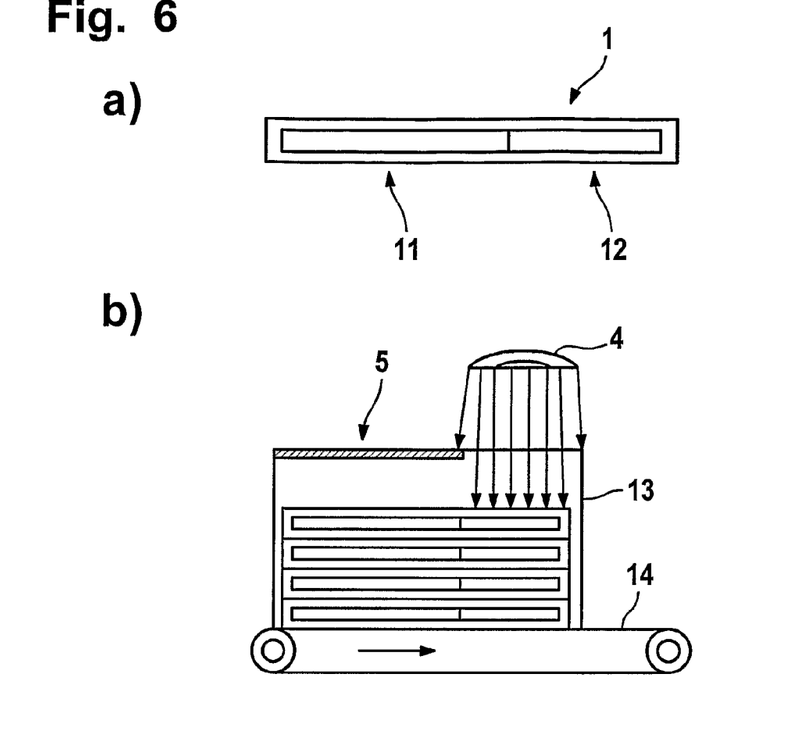
FIG. 6 Basic procedure for the selective sterilization of a diagnostic test element.

FIG. 6 illustrates the principle of selective sterilization. FIG. 6a shows a test element (1) which has a part to be protected (11) that should not be irradiated and a part to be irradiated (12) which should be sterilized by the electron radiation. FIG. 6b shows an example illustrating the principle of the irradiation process in an electron beam arrangement. The radiation (4) irradiates the part to be irradiated (12) of an arrangement of test elements (1) which are in an outer package (13) while the part to be protected (11) is screened by the screen (5). The test elements are moved into the radiation area on a transport tape (14). The screen (5) can be attached to the tape (14) or to the outer packaging (13).

The following figures illustrate the wide applicability of the method according to the invention to a wide variety of integrated test elements.

Figure 8:
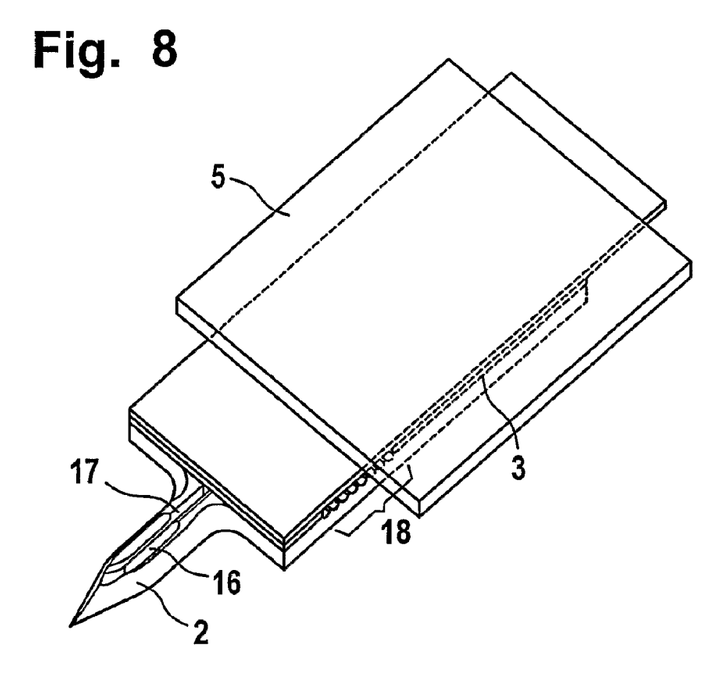
FIG. 8 Application of the selective sterilization to a lancing—measuring disposable with a so-called pooling area.

FIG. 8 shows the application of the method according to the invention to a lancing—measurement disposable. In this case the body fluid is collected in a so-called pooling area (16) during the lancing with the lancing area (2) and is transported via the capillary channel (17) and subchannels (18) into the detection area (3). The detection area (3) is screened during the selective sterilization by an overlying screen (5).

Figure 9:
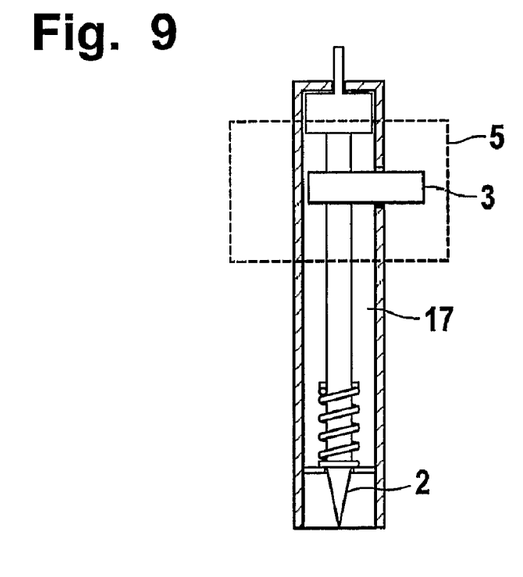
FIG. 9 Application of the selective sterilization to a diagnostic test element with a circular capillary gap.

FIG. 9 shows another possible application of the method according to the invention. In this case the body fluid is transported in a circular capillary gap (17) from the lancing area (2) to the detection area (3) during the lancing. The detection area (3) is screened by the screen (5) during the selective sterilization.

Figure 10:
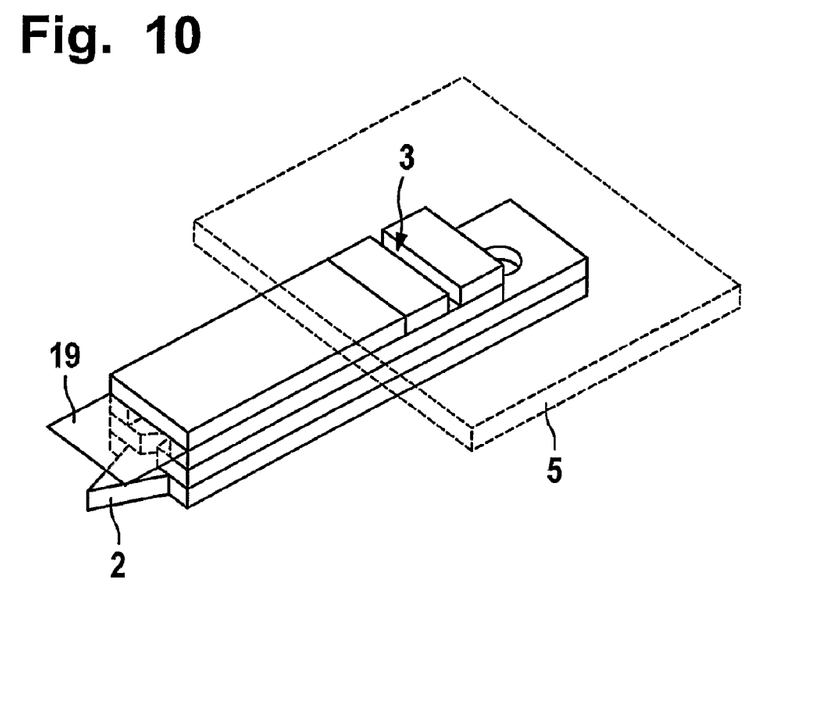
FIG. 10 Application of the selective sterilization to a diagnostic test element with a flexible collecting foil.

FIG. 10 shows another possible application of the method according to the invention. In addition to the lancing area (2) the integrated test element has a hydrophilic collecting foil (19) which hangs free over the lancing area and bends sideways during lancing and rests against the skin (20). After retracting the lancing area (2) from the skin (20), the body fluid from the skin opening (21) is transported along the collecting foil (19) into the capillary channel (17) and from there again into the detection area (3). The detection area (3) is screened by the screen (5) during the selective sterilization.

Figure 11:
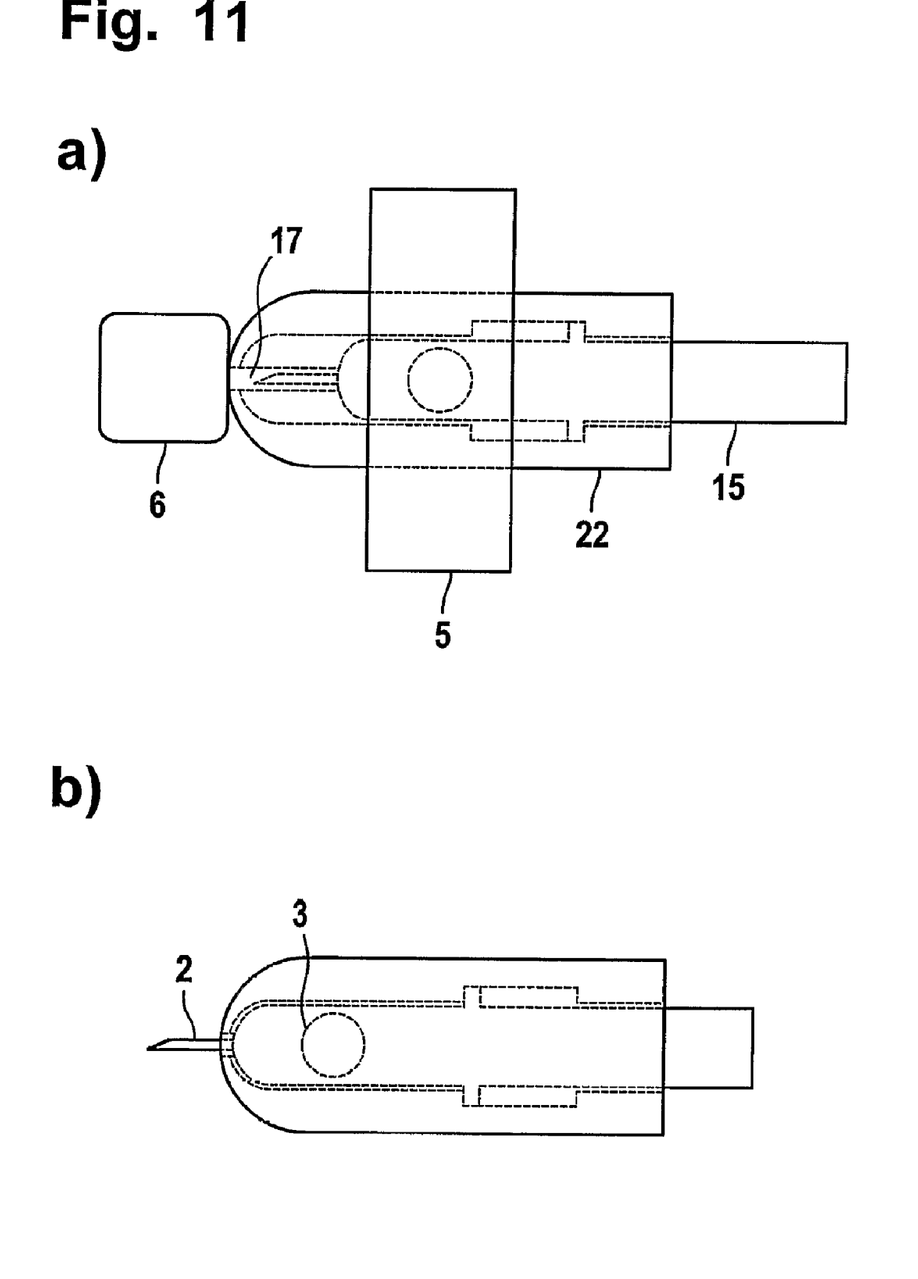
FIG. 11 Application of the selective sterilization to a diagnostic test element with a manually removable lancing area protection and a lancet that can be displaced relative to the test element base plate.

FIG. 11 shows another possible application of the method according to the invention. The protective cap (6) protects the lancing area (2) from contamination and is manually removed before use (FIG. 11a). The lancet (15) with the lancing area (2) is displaced during lancing relative to the test element base plate (22) (FIG. 11b) and subsequently again retracts into the base plate during which body fluid passes through the capillary channel (17) into the detection area (3). The detection area (3) is screened by the screen (5) during the selective sterilization in the production process.

The invention claimed is:

1. Method for producing integrated, diagnostic test elements which have a lancing area to generate an opening in the skin and a detection area to detect an analyte in a body fluid wherein the lancing area but not the detection area is sterilized by electron radiation, wherein the method comprises the steps screening the detection areas from electron radiation, wherein said screening includes packing the test elements in a package that has an integrated screen aligned with the detection areas of the test elements to screen the detection areas from the electron radiation; and subsequently irradiating the integrated screen and the package with the electron radiation to sterilize the lancing areas of the test elements.

2. Method according to claim 1, further comprising:

wherein the package includes a drum with a lower area coated with metal to act as the integrated screen; and wherein said packing includes loading the test elements into the drum with the detection areas received in the lower area coated with the metal and the lancing areas extending past the lower area coated with the metal.

3. Method according to claim 2, wherein said packing further includes individually arranging in an axially symmetric manner the test elements in chambers inside the drum.

4. Method according to claim 1, further comprising:

wherein the package includes a box;

wherein the screen includes a metal plate integrated into the box; and wherein said packing includes stacking the test elements in a matrix-like manner within the box with the detection areas screened by the metal plate.

5. Method according to claim 1, further comprising:

sealing the lancing area with a protection that prevents penetration of germs from the detection area and allows sterilization of the lancing area with electron radiation.

6. Method for producing integrated, diagnostic test elements which have a lancing area to generate an opening in the skin and a detection area to detect an analyte in a body fluid wherein the lancing area but not the detection area is sterilized by electron radiation, wherein the method comprises the steps sealing the detection area with a protective cover to create a barrier that prevents germs from the detection area from reaching the lancing area;

packing the test element into a package;

locating a radiation screen between the detection area of the test element and a source of electron radiation;

screening the detection area of the test element from electron radiation with the radiation screen;

irradiating the test element with the electron radiation after said screening; and locating the radiation screen at a location other than between the detection area and the source of electron radiation after said irradiating.

7. Method according to claim 6, wherein said packing occurs before said screening.

8. Method according to claim 6, wherein said packing includes sealing the test element in a plastic foil.

9. Method according to claim 6, wherein said packing includes packing the test elements inside in the package without additional protection for the lancing area.

10. Method according to claim 6, wherein said packing includes packing includes individually packing the test element within a primary packaging.

11. Method according to claim 10, wherein said individually packing the test element within the primary package includes sealing the test element within an individual chamber within the primary packaging.

12. Method according to claim 6, wherein said screening permits electron radiation to sterilize the lancing area.

13. Method for producing integrated, diagnostic test elements which have a lancing area to generate an opening in the skin and a detection area to detect an analyte in a body fluid wherein the lancing area but not the detection area is sterilized by electron radiation, wherein the method comprises the steps sealing the detection area with a protective cover to prevent the escape of germs to the lancing area while the lancing area remains exposed;

packing the test element into a package;

screening the detection area of the test element from electron radiation;

irradiating the test element with the electron radiation after said screening;

sterilizing the outside of the protective cover with plasma treatment;

wherein the package includes a drum with a lower area coated with metal to act as the integrated screen; and wherein said packing includes loading the test element into the drum with the detection area received in the lower area coated with the metal and the lancing area extending past the lower area coated with the metal.

14. Method for producing integrated, diagnostic test elements which have a lancing area to generate an opening in the skin and a detection area to detect an analyte in a body fluid wherein the lancing area but not the detection area is sterilized by electron radiation, wherein the method comprises the steps sealing the detection area in an air-tight manner with a protective cover to prevent the escape of germs to the lancing area while the lancing area remains exposed;

packing the test element into a package;

screening the detection area of the test element from electron radiation;

irradiating the test element with the electron radiation after said screening;

sterilizing the outside of the protective cover with plasma treatment;

wherein the package includes a box;

wherein the screen includes a metal plate integrated into the box; and wherein said packing includes stacking a plurality of the test elements in a matrix-like manner within the box with the detection areas screened by the metal plate.

* * * * *

UNITED STATES PATENT AND TRADEMARK OFFICE
CERTIFICATE OF CORRECTION

PATENT NO.         : 7,794,654 B2
APPLICATION NO.    : 11/620931
DATED              : September 14, 2010
INVENTOR(S)        : Karin Schwind et al.

It is certified that error appears in the above-identified patent and that said Letters Patent is hereby corrected as shown below:

Column 8, line 37, please change "with a partially irradiated test" to --with a partially irradiated test zone.--

Column 8, line 57, please change "numerals in the figures denote:" to --The numerals in the figures denote:--

Signed and Sealed this

Sixteenth Day of November, 2010

David J. Kappos
*Director of the United States Patent and Trademark Office*